United States Patent [19]

Floyd et al.

[11] 4,386,034
[45] May 31, 1983

[54] SULFAMATED AMINO ACID AMIDES

[75] Inventors: David M. Floyd, Pennington; Alan W. Fritz, Kendall Park; Christopher M. Cimarusti, Pennington, all of N.J.

[73] Assignee: E. R. Squibb & Sons, Inc., Princeton, N.J.

[21] Appl. No.: 347,595

[22] Filed: Feb. 10, 1982

Related U.S. Application Data

[62] Division of Ser. No. 230,837, Feb. 2, 1981.

[51] Int. Cl.³ .................................. C07C 143/68
[52] U.S. Cl. ........................ 260/456 A; 260/239 A
[58] Field of Search ............................ 260/456 A

[56] References Cited

FOREIGN PATENT DOCUMENTS 21678 1/1981 European Pat. Off. .

OTHER PUBLICATIONS

Miller et al., JACS, 102, 7026, (1980).
Crossland et al., J. Org. Chem., 26, 138, (1961).
Hoffmann, Synthesis, 1979, 699.
Gilbert, "Sulfonation & Related Reactions," Interscience, 1979, pp. 14, 413–414.

Primary Examiner—Nicky Chan
Attorney, Agent, or Firm—Lawrence S. Levinson; Donald J. Barrack

[57] ABSTRACT

The process of this invention provides for the conversion of amino acid amides having the formula

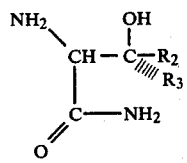

to 3-amino-2-oxo-1-azetidinesulfonic acid salts having the formula

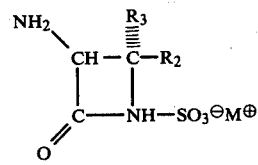

wherein one of $R_2$ and $R_3$ is hydrogen and the other is hydrogen, alkyl, cycloalkyl, phenyl or substituted phenyl and $M^\oplus$ is hydrogen or a cation.

2 Claims, No Drawings

SULFAMATED AMINO ACID AMIDES

This is a division of application Ser. No. 230,837, filed Feb. 2, 1981.

RELATED APPLICATION

U.S. patent application Ser. No. 226,562, filed Jan. 19, 1981, discloses novel β-lactam antibiotics. These products are zwitterions or salts of a β-lactam having a sulfonic acid substituent —$SO_3H$ in the 1-position and an acylamino substituent in the 3-position.

BRIEF DESCRIPTION OF THE INVENTION

It is an object of this invention to provide an efficient process operable under mild conditions, for the preparation of intermediates useful for the production of β-lactam antibiotics having the formula

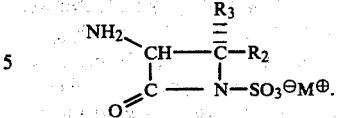

In formula I, and throughout the specification, the symbols are as defined below:
$R_1$ is acyl;
one of $R_2$ and $R_3$ is hydrogen and the other is hydrogen, alkyl, cycloalkyl, phenyl or substituted phenyl; and
$M^\oplus$ is hydrogen or a cation.

The process of this invention may be represented diagrammatically as follows:

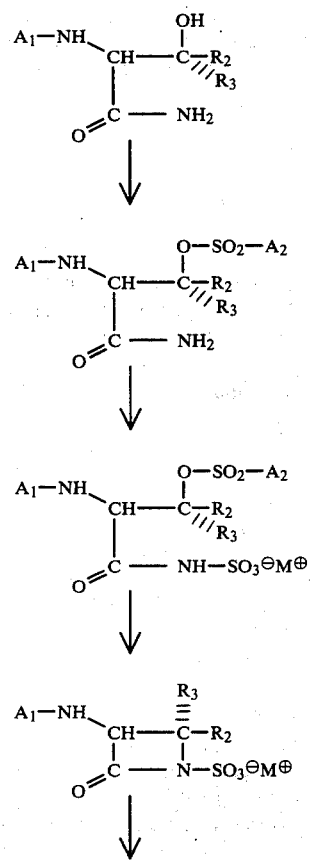

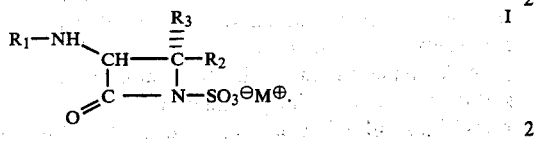

The compounds of formula IV are novel compounds, and as such, form an integral part of this invention. In the above structural formulas, and throughout the specification, the symbols $A_1$ and $A_2$ are as defined below.

$A_1$ is a nitrogen protecting group, e.g., alkylcarbonyl, arylcarbonyl, arylalkylcarbonyl, alkoxycarbonyl, or aryloxycarbonyl. Preferred groups are t-butoxycarbonyl and benzyloxycarbonyl.

$A_2$ is alkyl, phenyl or substituted phenyl (preferably methyl or 4-methylphenyl).

Listed below are definitions of various terms used to describe the β-lactams synthesized by this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3,4,5,6 or 7 carbon atoms.

The term "halogen" refers to fluorine, chlorine, bromine and iodine.

The term "aryl" refers to phenyl or substituted phenyl.

The term "substituted phenyl" refers to a phenyl group substituted with 1,2 or 3 halogen, trifluoromethyl, alkyl (of 1 to 4 carbon atoms), or alkoxy (of 1 to 4 carbon atoms) groups.

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, British Pat. No. 1,348,894, published Mar. 27, 1974, and U.S. patent application Ser. No. 226,562, filed Jan. 19, 1981. The portions of these references describing various acyl groups are incorporated herein by reference.

The term "cation," as used throughout the specification, refers to any positively charged atom or group of atoms. The "—$SO_3^\ominus M^\oplus$" substituent on the nitrogen atom of the β-lactams prepared by the process of this invention encompasses all sulfonic acid salts (including inner salts; i.e., $M^\oplus$ is hydrogen). Pharmaceutically acceptable salts are preferred (for the antibiotic products of formula I) while water-soluble salts are particularly useful in the process of this invention. The cationic portion of the —$SO_3^\ominus M^\oplus$ group can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

DETAILED DESCRIPTION OF THE INVENTION

The process of this invention is directed to the conversion of amino acid amides having the formula

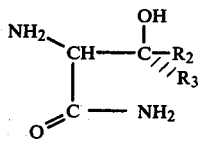   VII to 3-amino-2-oxo-1-azetidinesulfonic acid salts having the formula

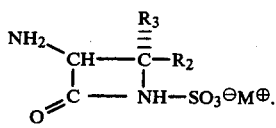   VIII

The compounds of formula VIII are useful as intermediates (convertible using conventional acylation techniques) for the preparation of β-lactam antibiotics of formula I. As described in U.S. patent application Ser. No. 226,562, filed Jan. 19, 1981, the β-lactam antibiotics of formula I can be used as agents to combat bacterial infections (including urinary tract infections and respiratory infections) in mammalian species, such as domesticated animals and humans. It is further disclosed that for combating bacterial infections in mammals a compound of formula I can be administered to a mammal in need thereof in an amount of about 1.4 mg/kg/day to about 350 mg/kg/day, preferably about 14 mg/kg/day to about 100 mg/kg/day.

The protected amino acid amides of formula II are readily obtainable from the corresponding amino acids using procedures well known in the art.

The first step of the process of this invention is the conversion of the hydroxyl group of a compound of formula II to a leaving group (i.e., $A_2-SO_2-O-$, preferably methanesulfonyloxy or p-toluenesulfonyloxy), yielding a compound having the formula

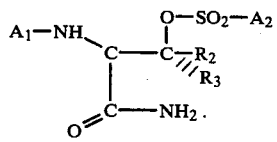   III

The conversion is accomplished by reacting a compound of formula II with a compound having the formula $$A_2-SO_2-X,$$   IX wherein X is chlorine or bromine. The reaction can be run in an organic solvent (e.g., pyridine or dichloromethane) in the presence of an organic base (e.g., triethylamine).

A compound of formula III can be sulfamated to yield novel intermediates having the formula

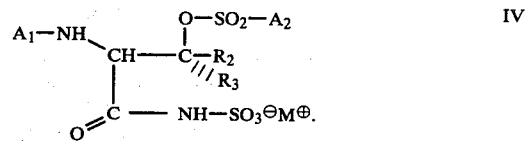   IV

Sulfamation of a compound of formula III will preferably be accomplished by treating a compound of formula III with a complex of sulfur trioxide and pyridine, and α-alkylpyridine, an α-alkyl-α'-alkylpyridine, or a trialkylamine (such as triethylamine). The preferred complexes are complexes of 2-picoline and sulfur trioxide and of 2,6-lutidine and sulfur trioxide. This choice of reagents allows the sulfamation reaction to be run under extremely mild conditions.

In one embodiment of this invention, the complex of sulfur trioxide and the pyridine can be formed in situ using a halosulfonic acid (chlorosulfonic acid is preferable) and the appropriate amine.

Cyclization of a compound of formula IV is accomplished by treating the compound with base. Because of the acidity of the proton of the $-NH-SO_3^\ominus M^\oplus$ group, it is possible to employ a weak base to accomplish the cyclization. Exemplary bases are alkali metal carbonates, bicarbonates, or hydroxides; quaternary ammonium carbonate, bicarbonate, or hydroxide; and tertiary amines. The reaction is preferably carried out in water or a mixture of water and an organic solvent (e.g., a halogenated hydrocarbon such as 1,2-dichloroethane), and yields a compound having the formula

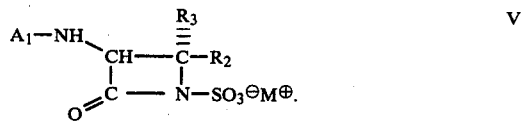   V

If water is used as the solvent the reaction is carried out at about 70° C. and if a biphasic solvent is used the reaction is carried out under reflux conditions.

Deprotection of a compound of formula V to obtain a compound having the formula

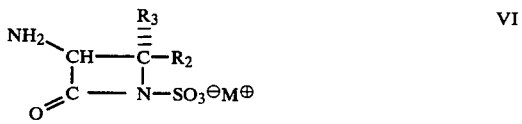   VI can be accomplished using known procedures that will depend on the particular protecting group ($A_1$) being removed. Treatment with acid (e.g., formic acid) cleaves a t-butoxycarbonyl protecting group. Treatment with hydrogen (using a catalyst such as palladium) cleaves a benzyloxycarbonyl protecting group. Treatment with phosgene or phosphorous pentachloride cleaves an amide protecting group.

The following examples are specific embodiments of this invention.

EXAMPLE 1

(S)-3-Amino-2-oxo-1-azetidinesulfonic acid (A) L-t-Butoxycarbonylserine amide mesylate A partial suspension of L-t-butoxycarbonylserine amide (16.2 g) in 250 ml of methylene chloride is cooled to $-10°$ C. and 10.4 ml of triethylamine is added. Methanesulfonyl chloride (4.25 ml) is added dropwise over a 15 minute period. After warming to 0° C., an additional 0.425 ml of methanesulfonyl chloride is added dropwise. After stirring at 0° C. for an additional 0.5 hour the reaction mixture is poured into 1 liter of ethyl acetate and 250 ml of cold brine is added. The resulting organic layer is further washed twice with 1 N HCl saturated with salt (200 ml), saturated sodium bicarbonate (250 ml) and finally with 250 ml of brine. The resulting ethyl acetate solution is dried over magnesium sulfate and concentrated to 100 ml. The resulting slurry is then diluted with 300 ml of diethyl ether and filtered to yield 10.73 g of the desired product. Concentration and recrystallization of the mother liquor affords an additional 1.67 g of product; melting point 105°–107° C., $[\alpha]_D^{21} = +6.4$ [c=2, methanol].

(B) L-tetra-n-Butylammonium t-butoxycarbonylserine sulfamate mesylate

Following the procedure of example 2B, but substituting L-t-butoxycarbonylserine amide mesylate for L-t-butoxycarbonylthreonine amide mesylate, yields the title compound.

(C) (S)-3-[(t-Butoxycarbonyl)amino]-2-oxo-1-azetidinesulfonic acid, tetra-n-butylammonium salt Following the procedure of example 2C, but substituting L-tetra-n-butylammonium t-butoxycarbonylserine sulfamate mesylate for L-tetra-n-butylammonium t-butoxycarbonylthreonine amide mesylate, yields the title compound.

(D) (S)-3-Amino-2-oxo-1-azetidinesulfonic acid (S)-3-[(t-Butoxycarbonyl)amino]-2-oxo-1-azetidinesulfonic acid, tetra-n-butylammonium salt (3.06 g) is dissolved in 18 ml of 97% formic acid, stirred for 4 hours, diluted with methylene chloride, filtered, washed and dried to give 0.52 g of the title compound; melting point 208°–210° C., dec.; $[\alpha]_D^{21} = -39.9$ [c=2, water].

EXAMPLE 2

(3S-trans)-3-Amino-4-methyl-2-oxo-1-azetidinesulfonic acid (A) L-t-Butoxycarbonylthreonine amide mesylate Using the procedure described in Example 1A, but substituting L-t-butoxycarbonylthreonine amide for L-t-butoxycarbonylserine amide, yields the title compound, melting point 129°–131° C., $[\alpha]_D^{21} = +18.9$ [c=10, methanol].

(B) L-tetra-n-Butylammonium t-butoxycarbonylthreonine sulfamate mesylate

A solution of 2-methylpyridine (17.8 ml) in 90 ml of methylene chloride is cooled to $-50°$ C. and 5.97 ml of chlorosulfonic acid is added at a rate which maintains the internal reaction temperature below 5° C. The resulting solution is stirred for 15 minutes and 8.9 g of L-t-butoxycarbonylthreonine amide mesylate is added as a solution in 30 ml of methylene chloride. The resulting solution is then refluxed for 16 to 20 hours and poured into 500 ml of 0.5 M potassium dihydrogen phosphate and further diluted with 120 ml of methylene chloride. The separated organic layer is washed with an additional 100 ml of phosphate solution and the combined aqueous phases are treated with 10.2 g of tetra-n-butylammonium hydrogensulfate and extracted with methylene chloride (one 300 ml portion and two 150 ml portions). The organic extracts are dried over sodium sulfate and concentrated to afford 17.2 g of the title compound as a foam.

(C) (3S-trans)-3-[(t-Butoxycarbonyl)amino]-4-methyl-2-oxo-1-azetidinesulfonic acid, tetra-n-butylammonium salt Potassium bicarbonate (13.0 g) is dissolved in 320 ml of water, 1,2-dichloroethane (220 ml) is added and the mixture is brought to reflux. L-tetra-n-Butlyammonium t-butoxycarbonylthreonine sulfamate mesylate (20.0 g) is added as a solution in 100 ml of 1,2-dichloroethane and the mixture is vigorously stirred under reflux for 15 minutes. The reaction mixture is poured into a separatory funnel and the lower, organic phase is separated. The aqueous layer is extracted with an additional 200 ml of methylene chloride and the combined organic phases are dried over sodium sulfate. Concentration yields 18 g of the title product in crude form, melting point 144°–146° C., $[\alpha]_D^{21} = -14.6$ [c−2, methanol].

(D) (3S-trans)-3-Amino-4-methyl-2-oxo-1-azetidinesulfonic acid (3S-trans)-3-[(t-Butoxycarbonyl)amino]-4-methyl-2-oxo-1-azetidinesulfonic acid tetra-n-butylammonium salt (6.3 g) is dissolved in 30 ml of 97% formic acid and stirred for 5 hours during which time a precipitate forms. The slurry is diluted with 30 ml of methylene chloride and filtered. The solids are further washed with methylene chloride and dried to yield 1.53 g of analytically pure product $[\alpha_D^{21} = -41.0$ [c=1, water].

EXAMPLE 3

(3S-trans)-3-Amino-4-methyl-2-oxo-1-azetidinesulfonic acid (A) L-Benzyloxycarbonylthreonine amide mesylate L-Benzyloxycarbonylthreonine amide (15.0 g) is dissolved in 90 ml of dry pyridine and the solution is cooled to $-5°$ C. and 7.05 ml of methanesulfonyl chloride is added slowly over a 5 minute period. After 2 hours the mixture is poured slowly into 750 ml of ice water with rapid stirring. The resulting slurry is stirred for 0.5 hour and filtered. The product is resuspended in 500 ml of water, refiltered and dried to yield 10.4 g of product, melting point 162°–164° C., $[\alpha]_D^{21} = +8.2$ [c=1, methanol].

(B) L-tetra-n-butylammonium benzyloxycarbonylthreonine sulfamate mesylate

Following the procedure of example 2B, but substituting L-benzyloxycarbonylthreonine amide mesylate for L-t-butoxycarbonylthreonine amide mesylate, yields the title compound.

(C) (3S-trans)-3-[(Benzyloxycarbonyl)amino]-4-methyl-2-oxo-1-azetidinesulfonic acid, tetra-n-butylammonium salt Following the procedure described in example 2C, but substituting L-tetra-n-butylammonium benzyloxycarbonylthreonine sulfamate mesylate for L-tetra-n-butylammonium-t-butoxycarbonylthreonine sulfamate mesylate, yields the title compound.

(D) (3S-trans)-3-Amino-4-methyl-2-oxo-1-azetidinesulfonic acid (3S-trans)-3-[(Benzyloxycarbonyl)amino]-4-methyl-2-oxo-1-azetidinesulfonic acid tetra-n-butylammonium salt is dissolved in 250 ml of ethanol and 0.8 g of 5% palladium on charcoal is added. Hydrogen is bubbled through the stirred mixture for 90 minutes and the catalyst is filtered out. The addition of 12 ml of formic acid causes an immediate precipitation of the title compound which is filtered and dried. A second crop of the title compound is obtained upon concentration of the filtrate and the addition of more formic acid, yielding a total of 1.3 g of the title compound.

EXAMPLE 4

(3S-trans)-3-Amino-4-methyl-2-oxo-1-azetidinesulfonic acid (A) L-Phenylacetylthreonine amide mesylate A solution of L-phenylacetylthreonine amide (16.9 g) in 500 ml of tetrahydrofuran is prepared by heating to reflux to effect solution and then cooling to $-35°$ C. To this cold solution 15.0 ml of triethylamine is added followed by 7.1 ml of methanesulfonyl chloride over a 1 hour period. The reaction mixture is stirred for an additional 1 hour and diluted with 400 ml of water; the organic layer separates. The aqueous layer is then extracted with ethyl acetate (three 300 ml portions). The combined organic phases are washed with 0.1 N HCl in brine, with brine and dried over magnesium sulfate. Filtration and concentration to about 200 ml causes precipitation of the product. The slurry is diluted with an equal volume of hexane and filtered to afford 19.2 g of product, melting point 132°–133° C., $[\alpha]_D^{21} = +19.25 [c=2$, methanol].

(B) L-tetra-n-butylammonium phenylacetylthreonine sulfamate mesylate

Following the procedure of example 2B, but substituting L-phenylacetylthreonine amide mesylate for L-t-butoxycarbonylthreonine amide mesylate, yields the title compound.

(C) (3S-trans)-3-[(Phenylacetyl)amino]-4-methyl-2-oxo-1-azetidinesulfonic acid, tetrabutylammonium salt Following the procedure described in example 2C, but substituting L-tetra-n-butylammonium phenylacetylthreonine sulfamate mesylate for L-tetra-n-butylammonium t-butoxycarbonylthreonine sulfamate mesylate, yields the title compound.

(D) (3S-trans)-3-Amino-4-methyl-2-oxo-1-azetidinesulfonic acid (3S-trans)-3-[(Phenylacetyl)amino]-4-methyl-2-oxo-1-azetidinesulfonic acid, tetra-n-butylammonium salt (3.79 g) is dissolved in 70 ml of methylene chloride, cooled to $-15°$ C. and 2.3 ml of pyridine is added. The cold mixture is treated with 5.8 ml of a 12% mixture of phosgene in benzene and stirred at $-10°$ C. for 90 minutes. Methanol (35 ml) is added and the mixture is stirred for 30 minutes followed by the addition of 1.62 ml of trifluoroacetic acid. The reaction mixture is allowed to warm to room temperature and stirred for 16 hours. The precipitated material is collected by filtration, washed with methylene chloride and dried to yield 0.43 g of the title compound.

EXAMPLE 5

(3S-cis)-3-Amino-4-methyl-2-oxo-1-azetidine sulfonic acid (A) L-t-Butoxycarbonyl-allo-threonine amide mesylate Following the procedure described in Example 1A, but substituting L-t-butoxycarbonyl-allo-threonine amide for L-t-butoxycarbonylserine amide, yields the title compound, melting point 124° C., dec., $[\alpha]_D^{21} = +16.9 ]c=2$, methanol].

(B) L-tetra-n-Butylammonium t-butoxycarbonyl-allo-threonine sulfamate mesylate

Following the procedure of example 2B, but substituting L-t-butoxycarbonyl-allo-threonine amide mesylate for L-t-butoxycarbonylthreonine amide mesylate, yields the title compound.

(C) (3S-cis)-3-[(t-Butoxycarbonyl)amino]-4-methyl-2-oxo-1-azetidinesulfonic acid, tetra-n-butylammonium salt Following the procedure described in example 2C, but substituting L-tetra-n-butylammonium t-butoxycarbonyl-allo-threonine sulfamate mesylate for L-tetra-n-butylammonium t-butoxycarbonylthreonine sulfamate mesylate, yields the title compound.

(D) (3S-cis)-3-Amino-4-methyl-2-oxo-1-azetidinesulfonic acid

Following the procedure of example 2D, but substituting (3S-cis)-3-[(t-butoxycarbonyl)-amino]-4-methyl-2-oxo-1-azetidinesulfonic acid, tetrabutylammonium salt for (3S-trans)-3-[(t-butoxycarbonyl)amino]-4-methyl-2-oxo-1-azetidinesulfonic acid, tetrabutylammonium salt yields the title compound, melting point 200° C., dec., $[\alpha]_D^{21} = -61.8°[c=5.1$, water].

What is claimed is:

1. A compound having the formula

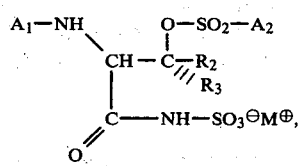

wherein $A_1$ is alkylcarbonyl, arylcarbonyl, alkoxycarbonyl or aryloxycarbonyl; $A_2$ is alkyl, phenyl, or substituted phenyl, one of $R_2$ and $R_3$ is hydrogen and the other is hydrogen, alkyl, cycloalkyl, phenyl or substituted phenyl; and $M^\oplus$ is a cation.

2. A compound in accordance with claim 1 wherein one of $R_2$ and $R_3$ is hydrogen and the other is methyl.

* * * * *